US00PP21685P3

(12) United States Plant Patent

Ackerman et al.

(10) Patent No.: US PP21,685 P3

(45) Date of Patent: Feb. 1, 2011

(54) RASPBERRY PLANT NAMED 'ELEGANCE'

(50) Latin Name: *Rubus idaeus*
Varietal Denomination: Elegance

(75) Inventors: Stephen M. Ackerman, Salinas, CA (US); Scott W. Adams, Watsonville, CA (US)

(73) Assignees: Plant Sciences, Inc., Watsonville, CA (US); Berry R&D, Inc., Watsonville, CA (US)

( * ) Notice: Subject to any disclaimer, the term of this patent is extended or adjusted under 35 U.S.C. 154(b) by 12 days.

(21) Appl. No.: 12/462,273

(22) Filed: Jul. 31, 2009

(65) Prior Publication Data

US 2010/0218291 P1 Aug. 26, 2010

Related U.S. Application Data

(60) Provisional application No. 61/154,201, filed on Feb. 20, 2009.

(51) Int. Cl.
*A01H 5/00* (2006.01)

(52) U.S. Cl. ..... Plt./204

(58) Field of Classification Search ..... Plt./204

See application file for complete search history.

(56) References Cited

U.S. PATENT DOCUMENTS

PP10,142 P * 12/1997 Ackerman ..... Plt./204
PP15,151 P3 * 9/2004 Ackerman ..... Plt./204

* cited by examiner

*Primary Examiner*—Wendy C. Haas
(74) *Attorney, Agent, or Firm*—Foley & Lardner LLP

(57) ABSTRACT

This invention relates to a new and distinct everbearing variety of raspberry plant named 'ELEGANCE'. The new variety is primarily adapted to the growing conditions of the central coast of California and is characterized by the following: firm, glossy medium-red fruit of conic shape, even color, and very good flavor. Foliage is slightly to strongly concave, medium green; possessing medium to strong rugosity and mostly 3-foliate. Primocanes have a weak waxy coat, medium thorn density, and weak anthocyanin coloration. Time of production of the floricane crop is early.

4 Drawing Sheets

Latin name of the genus and species of the plant claimed: *Rubus idaeus*.

Variety denomination: 'ELEGANCE'.

BACKGROUND OF THE INVENTION

The present invention relates to a new and distinct fall bearing raspberry variety designated as 'ELEGANCE'. This new variety is a result of a controlled cross made in 2001 between raspberry variety 'PS-1703' (patented, U.S. Plant Pat. No. 15,151) and raspberry variety 'PS-1720' (unpatented) in an ongoing breeding program. The variety is botanically known as *Rubus idaeus*.

The seedling resulting from the aforementioned cross was asexually propagated by dormant canes in Santa Cruz County, Calif., and was subsequently selected by the inventors from a controlled breeding plot in Watsonville, Calif. in 2003. After its selection, the new variety was further asexually propagated by dormant canes, roots and non-dormant root shoot cuttings in Santa Cruz County, Calif., San Joaquin County, Calif. and Siskiyou County, Calif. The new variety was then extensively tested over the next several years in fruiting fields in Santa Cruz County, Calif. This propagation has demonstrated that the combination of traits disclosed herein as characterizing the new variety are fixed and remain true to type through successive generations of asexual reproduction.

BRIEF SUMMARY OF THE INVENTION

'ELEGANCE' is primarily adapted to the climate and growing conditions of the central coast of California. This region provides the necessary year-round temperatures required for it to produce and maintain a strong vigorous plant and to remain in fruit production from July through December on primocanes and in the ensuing year from May through July on the floricanes. The following traits have been repeatedly observed and are determined to be unique characteristics of 'ELEGANCE', which in combination distinguish this raspberry plant as a new and distinct variety:

1. Early floricane time of fruiting;
2. Weak primocane glaucosity;
3. Light brown floricane color;
4. Predominant leaflet number of 3; and
5. Strong fruit gloss.

The raspberry varieties that are believed to be most closely related to the new raspberry variety 'ELEGANCE' are the raspberry variety 'PS-1049' (patented, U.S. Plant Pat. No. 10,142), and the parental, raspberry variety 'PS-1703' (patented, U.S. Plant Pat. No. 15,151). In comparison to the similar raspberry varieties 'PS-1049' and 'PS-1703', 'ELEGANCE' differs by the following combination of characteristics described in Table 1:

TABLE 1

| Characteristic | 'ELEGANCE' | 'PS-1049' (US PP10,142) | 'PS-1703' (US PP15,151) |
|---|---|---|---|
| 1. Primocane waxy coat (glaucosity) | Weak | Strong | Ranges from medium to strong |
| 2. Predominate number of leaflets | Mostly 3 | Equal 3-5 | Mostly 5 |
| 3. Floricane time of fruiting | Early | Medium | Medium |
| 4. Floricane color | RHS 161C Greyed-yellow group | RHS 166C Greyed-orange group | RHS 164A Greyed-orange group |
| 5. Primocane lateral length (cm) | 25.8 | 35.6 | 48.8 |
| 6. Primocane % of cane length fruiting | 37% | 42% | 52% |
| 7. Primocane color | RHS 145A Yellow-green group | RHS 154C Yellow-green group | RHS 145D Yellow-green group |
| 8. Color mature fruit | RHS 47B Red group | RHS 46A Red group | RHS 53A Red group |
| 9. Gloss mature fruit | Strong | Medium | Strong |

For identification, a series of AFLP molecular markers have been determined for this new variety.

BRIEF DESCRIPTIONS OF THE PHOTOGRAPHS

The accompanying color photographs illustrate the overall appearance of typical specimens of the new raspberry variety, 'ELEGANCE' at various stages of development as true as reasonably possible with color reproductions of this type. Color in the photographs may differ slightly from the color value cited in the detailed botanical description which accurately describes the color of 'ELEGANCE'. The depicted plant and plant parts of the new raspberry variety 'ELEGANCE' were taken in Watsonville, Calif. and are approximately 2 to 16 months old:

FIG. 1. shows typical primocane foliage and fruit color; foliate and rugosity characteristics of 'ELEGANCE', taken in the month of August 2008;

DETAILED BOTANICAL DESCRIPTION

Figure 1:
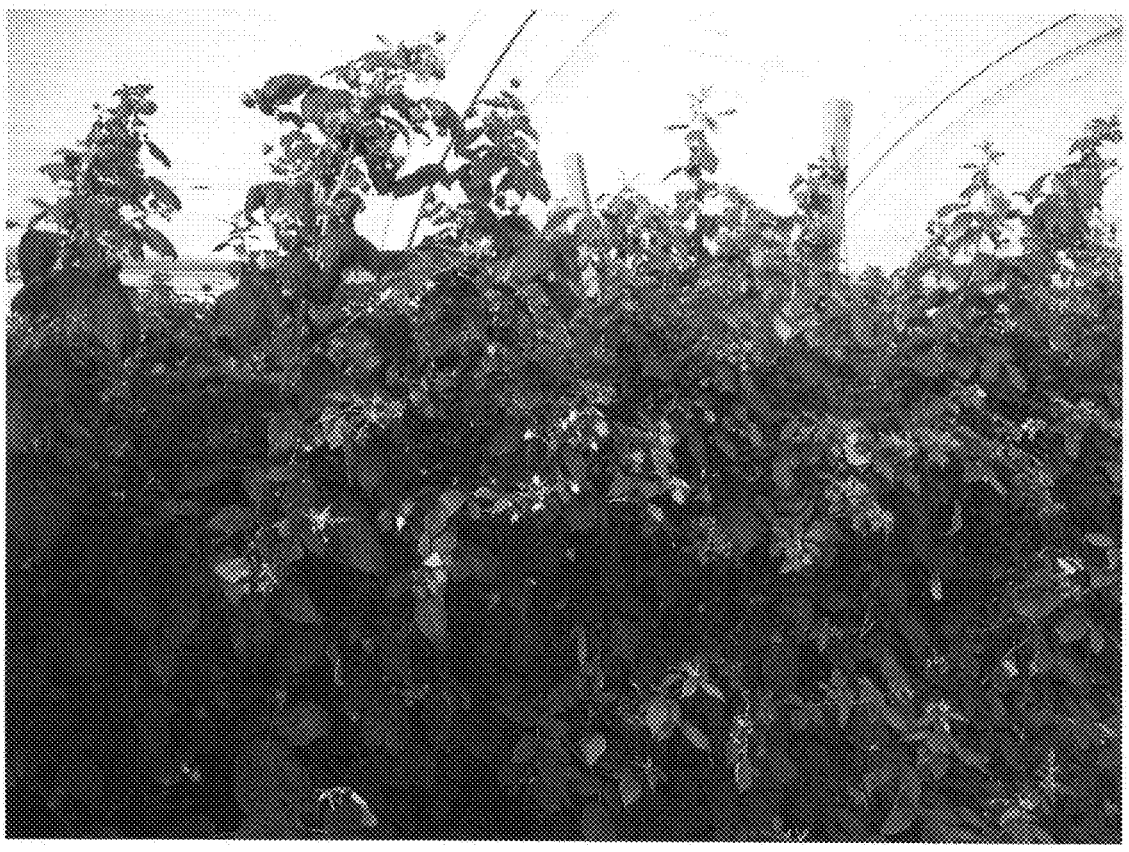
Figure 2:
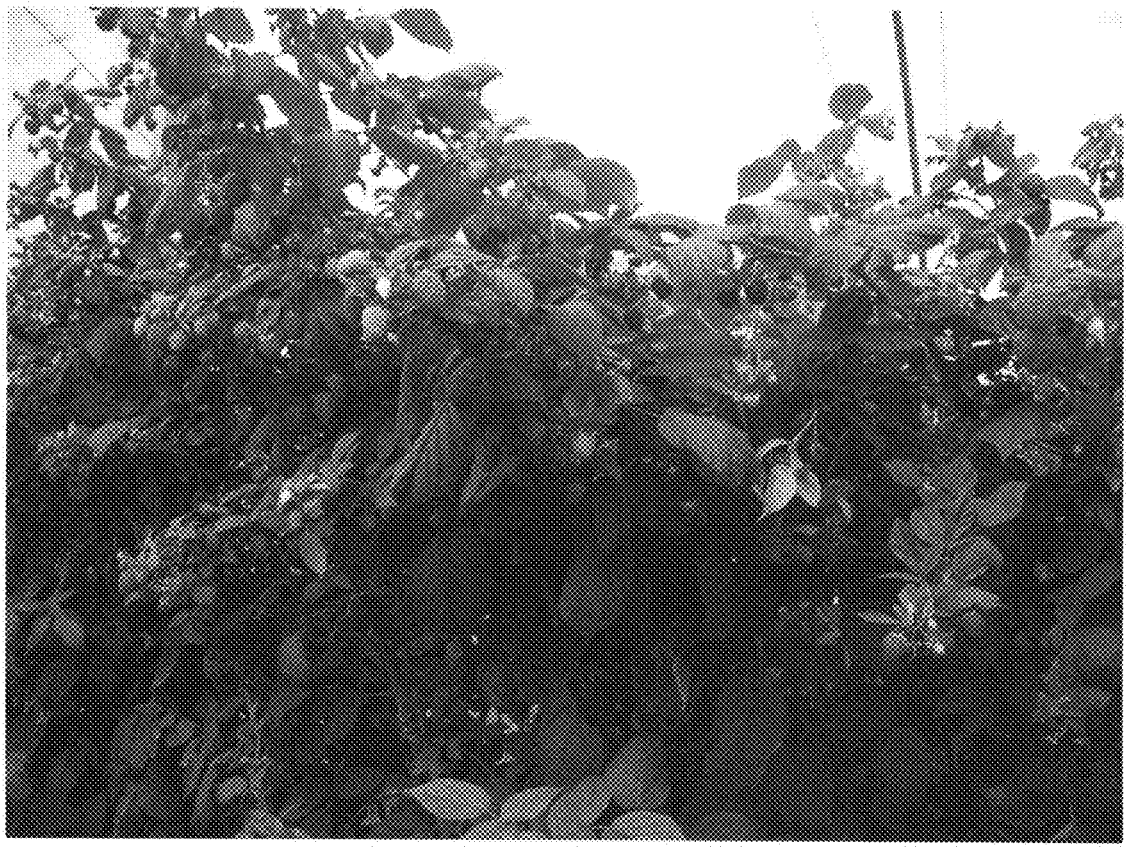
FIG. 2 shows typical primocane foliage and fruit color; foliate and rugosity characteristics of 'ELEGANCE', taken in the month of September 2008.
Figure 3:
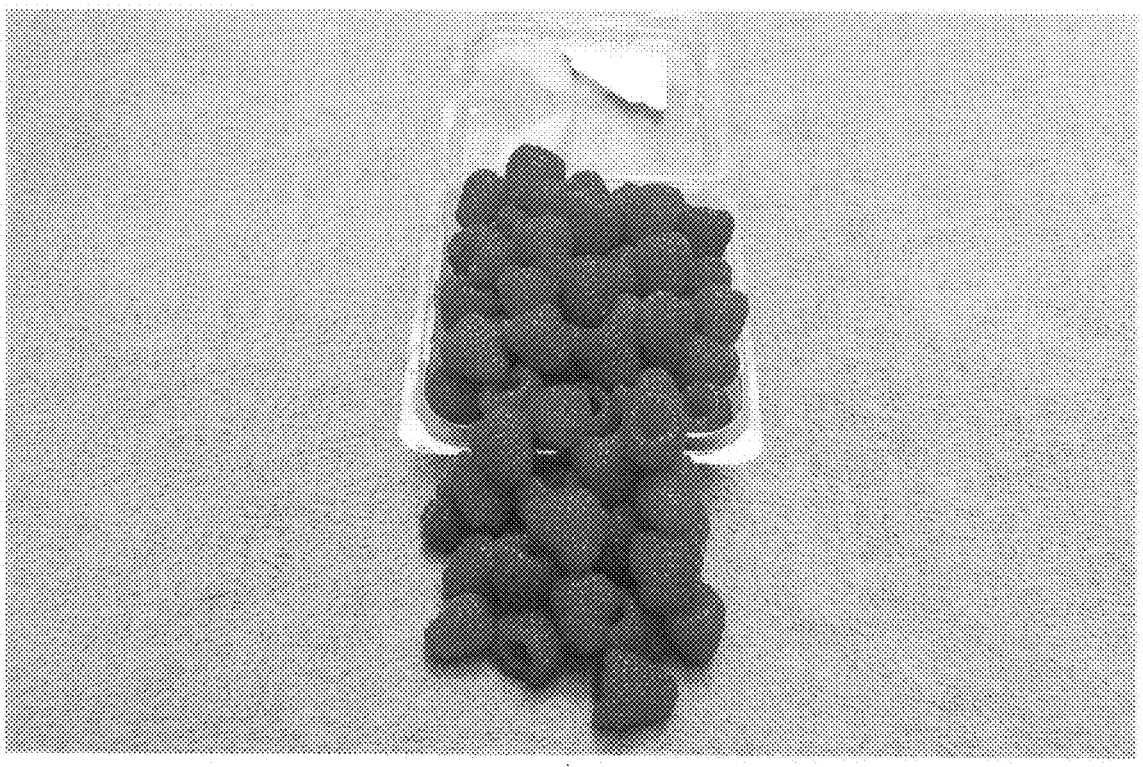
FIG. 3 shows typical harvested fruit of 'ELEGANCE', taken in the month of July 2009.
Figure 4:
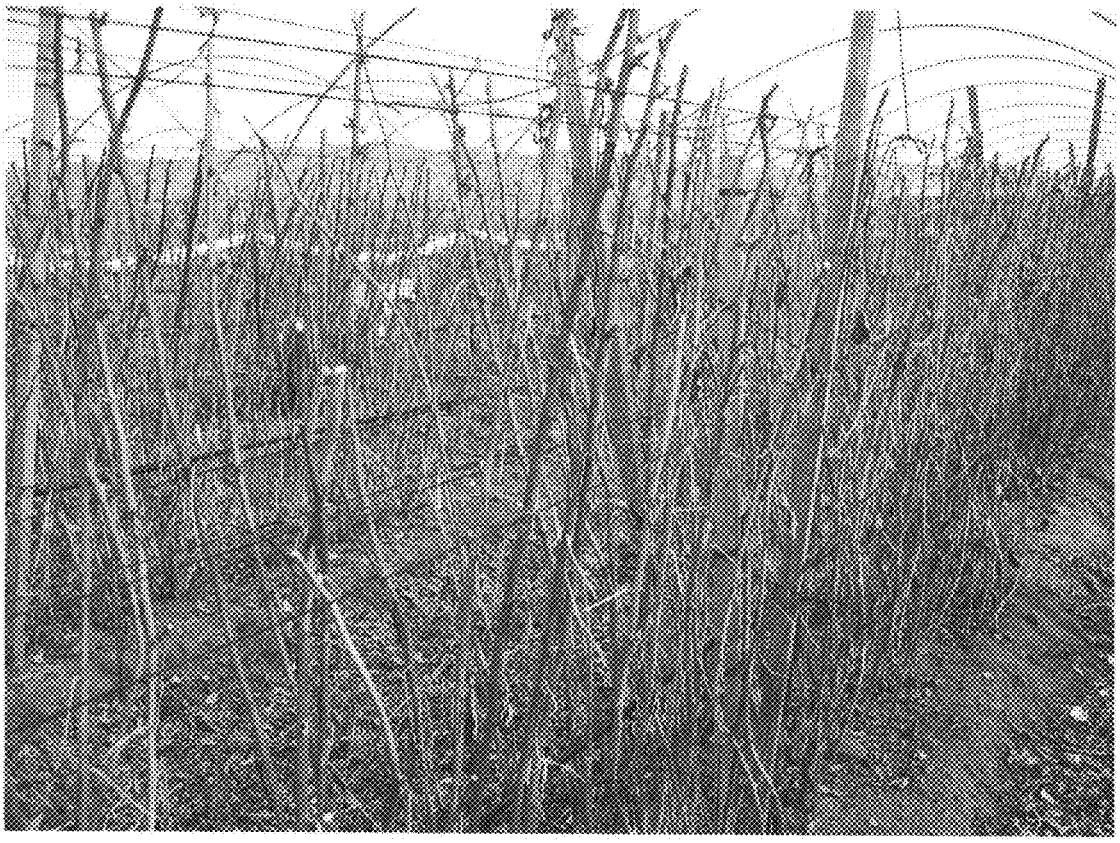
FIG. 4 shows typical dormant cane color characteristics of 'ELEGANCE', taken in the month of February 2007.

'ELEGANCE' has not been observed under all possible environmental conditions. The characteristics of the new variety may vary in detail, depending upon variations in environmental factors, including weather (temperature, humidity and light intensity), day length, soil type, and location.

The aforementioned photographs, together with the following description of the new raspberry variety 'ELEGANCE', unless otherwise noted, are based upon observations taken during the 2008 to 2009 growing season in Watsonville, Calif. Primocane measurements and ratings were taken from plants of 'ELEGANCE' dug from a nursery located in Siskiyou County, Calif. during the middle of October 2007 and planted approximately 7 to 8 weeks later in Watsonville, Calif. The approximate age of the observed primocane plants is 7 to 8 months. Floricane measurements and ratings were taken from the same planting of 'ELEGANCE' at an approximate age of 16 to 18 months. Yield observations and fruit quality characteristics are averaged from three years of data collected from the 2006 through 2008 production seasons. Flower measurements and characteristics are from secondary flowers unless otherwise noted. Fruit characteristics and measurements are from secondary fruit unless otherwise noted. Foliage characteristics and measurements are from 3-foliate foliage unless otherwise noted.

Color terminology where noted follows The R.H.S. Colour Chart, Royal Horticultural Society, London, England 2007.

The following Tables 2-6 describe fruit, plant, foliage, flower and pest/disease characteristics of the new raspberry 'ELEGANCE' in comparison to the similar raspberry varieties 'PS-1049' (patented, U.S. Plant Pat. No. 10,142) and 'PS-1703' (patented, U.S. Plant Pat. No. 15,151).

TABLE 2

FRUIT CHARACTERISTICS

| Characteristic | 'ELEGANCE' | 'PS-1049' (US PP10,142) | 'PS-1703' (US PP15,151) |
|---|---|---|---|
| Color mature fruit | RHS 47B Red group | RHS 46A Red group | RHS 53A Red group |
| Color achenes | RHS 164D Greyed-orange group | RHS 164D Greyed-orange group | RHS 164D Greyed-orange group |
| Fruit Length (cm) | 1.9 | 1.9 | 2.0 |
| Fruit Width (cm) | 1.8 | 1.8 | 1.9 |
| Length/Width Ratio | 1.0 Slightly longer than broad | 1.1 Slightly longer than broad | 1.1 Slightly longer than broad |
| Seed weight (mg) | 1.4 | 1.5 | 1.5 |
| Druplets per berry | 70 | 73 | 78 |
| Fruit size | Medium | Medium | Medium |
| Predominant shape | Conical | Conical | Conical |
| Evenness of color | Even | Even | Even |
| Glossiness | Strong | Medium | Strong |
| Adherence to receptacle | Weak to medium | Weak | Weak |
| Firmness of flesh | Very firm | Very firm | Firm |
| Firmness of skin | Very firm | Very firm | Medium |
| Soluble Solids (% brix) | 9.5 | 9.2 | 10.3 |
| Flavor | Very Good | Good | Excellent |

TABLE 3

| PLANT CHARACTERISTICS | | | |
|---|---|---|---|
| Characteristic | 'ELEGANCE' | 'PS-1049' (US PP10,142) | 'PS-1703' (US PP15,151) |
| General: | | | |
| Habit | Upright | Semi-upright | Semi-upright |
| Size | Medium | Medium | Medium |
| Productivity | Medium to high | Medium to high | High |
| Self fruitfulness | Yes | Yes | Yes |
| Type of bearing | Everbearing | Everbearing | Everbearing |
| Primocane: | | | |
| Color | RHS 145A Yellow-green group | RHS 154C Yellow-green group | RHS 145D Yellow-green group |
| Length (m) | 1.9 | 1.7 | 1.6 |
| Basal diameter (mm) | 12.1 | 14.8 | 12.4 |
| Diameter central 1/3 (mm) | 11.0 | 11.9 | 11.4 |
| Lateral length (cm) | 25.8 | 35.6 | 48.8 |
| No. fruiting laterals per cane | 20 | 16 | 19 |
| % of cane length fruiting | 37% | 42% | 52% |
| Internode length at central 1/3 (cm) | 5.8 | 5.2 | 4.8 |
| Anthocyanin coloration | RHS 59B | RHS 59C | RHS 59B |
| Anthocyanin intensity | Weak | Weak to medium | Medium to strong |
| Pubescence | Absent | Absent | Absent |
| Length of vegetative bud | Short | Medium to short | Medium to short |
| Strength of waxy coat | Weak | Strong | Ranges from medium to strong |
| Time of flowering | Medium | Medium | Early |
| Time of fruiting | Medium | Medium | Early |
| Length of fruiting season | Long | Long | Long |
| % of total yield | 42% | 47% | 47% |
| Flowering period | Late June to late November | Late June to late November | Early June to late November |
| Harvest period | Late July to late December | Late July to late December | Early July to late December |
| Primocane fruit weight (g) | 2.6 | 2.6 | 2.9 |
| Primocane yield (g/plant) | 1,587 | 1,862 | 2,241 |
| Young Shoots: | | | |
| Number | Medium | Medium | Medium |
| Anthocyanin coloration | Present | Present | Present |
| Anthocyanin intensity | Weak to medium | Very weakto weak | Weak to medium |
| Thorns: | | | |
| Color | RHS 59B Red-purple group | RHS 59B Red-purple group | RHS 59B Red-purple group |
| Length at central 1/3 (mm) | 1.5 | 2.4 | 1.8 |
| Presence on cane | Present | Present | Present |
| Density on cane | Medium | Medium | Medium to dense |
| Texture | Rigid | Rigid | Rigid |
| Attitude of the tip | Horizontal | Horizontal | Horizontal |
| Floricane: | | | |
| Color | RHS 161C Greyed-yellow group | RHS 166C Greyed-orange group | RHS 164A Greyed-orange group |
| Length (M) | 1.5 | 1.3 | 1.3 |
| Length vegetative bud | Short | Medium to short | Medium to short |
| Strength of waxy coat (glaucosity) | Weak | Strong | Ranges from medium to strong |
| Fruiting lateral attitude | Erect to semi-erect | Erect to semi-erect | Horizontal to drooping |
| Time of bud burst | Medium-Early | Medium | Medium |
| Time of flowering | Medium-Early | Medium | Medium |
| Time of fruiting | Early | Medium | Medium |
| Length of fruiting season | Medium to long | Medium to long | Medium to long |
| % of total yield | 58% | 53% | 53% |
| Flowering period | Late March to Late June | Late April to Late June | Mid April to Late June |

TABLE 3-continued

| PLANT CHARACTERISTICS | | | |
|---|---|---|---|
| Characteristic | 'ELEGANCE' | 'PS-1049' (US PP10,142) | 'PS-1703' (US PP15,151) |
| Harvest period | Mid April to Late July | Late May to Late July | Early May to Late July |
| Floricane fruit weight (g) | 2.7 | 2.5 | 2.9 |
| Floricane yield (g/plant) | 2,199 | 2,145 | 2,497 |

TABLE 4

| FOLIAGE CHARACTERISTICS | | | |
|---|---|---|---|
| Characteristic | 'ELEGANCE' (3 Foliate) | 'PS-1049' (US PP10,142) (3 Foliate) | 'PS-1703' (US PP15,151) (5 Foliate) |
| General: | | | |
| Color of upper surface | RHS 139A Green group | RHS 138A Green group | RHS N137A Green group |
| Color of lower surface | RHS 190B Greyed-green group | RHS 190C Greyed-green group | RHS 190B Greyed-green group |
| Shape in cross section | Ranges from slightly concave to strongly concave | Slightly concave | Ranges from slightly convex to slightly concave |
| Arrangement | Compound | Compound | Compound |
| Relief between veins | Medium to strong | Medium | Medium to strong |
| Glossiness | Weak | Weak | Medium |
| Number of leaflets/leaf | Mostly 3 | Equal 3-5 | Mostly 5 |
| Terminal Leaflet: | | | |
| Length(cm) | 11.1 | 12.2 | 10.7 |
| Width (cm) | 7.2 | 8.0 | 5.3 |
| Length/Width Ratio | 1.5 Longer than broad | 1.5 Longer than broad | 2.0 Much longer than broad |
| Size | Medium to large | Medium to large | Medium to small |
| Shape | Lobed cordate | Cordate | Lobed oblique |
| Shape of base | Cordate | Cordate | Acute |
| Shape of tip | Acuminate | Acuminate | Acuminate |
| Margins | Biserrate | Biserrate | Biserrate |
| Lateral Leaflet: | | | |
| Length (cm) | 9.2 | 9.9 | 9.5 |
| Width (cm) | 5.6 | 6.1 | 5.5 |
| Rachis length (cm) | 1.6 | 2.8 | 1.7 |
| Orientation | Opposite | Opposite | Opposite |
| Arrangement | Compound | Compound | Compound |
| Shape | Ovate | Ovate | Oblique |
| Overlapping | Touching | Touching | Free |
| Shape of the base | Acute obtuse | Oblique rounded | Acute oblique |
| Shape of the tip | Acuminate | Acuminate | Acuminate |
| Margins | Biserrate | Biserrate | Biserrate |
| Petiole: | | | |
| Length (cm) | 3.9 | 4.4 | 5.3 |
| Width (mm) | 2.7 | 2.4 | 2.7 |
| Thorn presence | Yes | Yes | Yes |
| Thorn orientation | Erect | Erect | Erect |
| Anthocyanin coloration of upper surface | Red-purple RHS 60A | Red-purple RHS 58A | Greyed-purple RHS 187B |
| Intensity of anthocyanin coloration | Weak | Weak | Strong |
| Pigmentation of lower surface | Yellow-green RHS 145B | Yellow-green RHS 145C | Yellow-green RHS 145C |
| Stipule length (cm) | 0.9 | 0.9 | 0.9 |
| Stipule orientation | Erect | Erect | Erect |

TABLE 5

| FLOWER CHARACTERISTICS | | | |
|---|---|---|---|
| Characteristic | 'ELEGANCE' | 'PS-1049' (US PP10,142) | 'PS-1703' (US PP15,151) |
| Petal color | RHS 155C White group | RHS 155C White group | RHS 155C White group |
| Flower diameter (cm) | 1.6 | 1.8 | 1.5 |
| Petal Length (mm) | 6.4 | 6.1 | 6.0 |
| Petalwidth(mm) | 3.2 | 3.1 | 3.0 |
| Petal length/width ratio | 2.0 Much longer than broad | 2.0 Much longer than broad | 2.0 Much longer than broad |
| No. petals/flower | 5.2 | 5.1 | 5.3 |
| No. sepals/flower | 5.2 | 5.1 | 5.3 |
| Pedicel no. spines | Many | Many | Medium |
| Peduncle anthocyanin presence | Present | Present | Present |
| Peduncle anthocyanin color | RHS 60A Red-purple group | RHS 59C Red-purple group | RHS 187C Greyed-purple group |
| Peduncle anthocyanin intensity | Weak | Very weak | Weak |

TABLE 6

| PEST AND DISEASE REACTIONS | | | |
|---|---|---|---|
| Characteristic | 'ELEGANCE' | 'PS-1049' (US PP10,142) | 'PS-1703' (US PP15,151) |
| Two spotted spider mite | Susceptible | Susceptible | Susceptible |
| Grey fruit mold | Susceptible | Susceptible | Susceptible |
| Powdery mildew | Moderately Susceptible | Moderately Susceptible | Moderately Susceptible |
| Yellow rust | Moderately Resistant | Moderately Susceptible | Moderately Resistant |

What is claimed is:

1. A new and distinct *Rubus idaeus* variety of raspberry plant named 'ELEGANCE', as herein described and illustrated by the characteristics set forth above.

* * * * *